United States Patent
Kerber

(10) Patent No.: US 11,212,625 B2
(45) Date of Patent: Dec. 28, 2021

(54) ADAPTIVE NOISE CANCELLING OF BONE CONDUCTED NOISE IN THE MECHANICAL DOMAIN

(71) Applicant: MED-EL Elektromedizinische Geraete GmbH, Innsbruck (AT)

(72) Inventor: Martin J. Kerber, Weer (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 3 days.

(21) Appl. No.: 16/338,779

(22) PCT Filed: Nov. 1, 2017

(86) PCT No.: PCT/US2017/059444
§ 371 (c)(1),
(2) Date: Apr. 2, 2019

(87) PCT Pub. No.: WO2018/085328
PCT Pub. Date: May 11, 2018

(65) Prior Publication Data
US 2020/0296522 A1    Sep. 17, 2020

Related U.S. Application Data

(60) Provisional application No. 62/415,560, filed on Nov. 1, 2016.

(51) Int. Cl.
*H04R 25/00* (2006.01)
*A61N 1/36* (2006.01)

(52) U.S. Cl.
CPC ......... *H04R 25/43* (2013.01); *A61N 1/36038* (2017.08); *H04R 2410/05* (2013.01); *H04R 2460/13* (2013.01)

(58) Field of Classification Search
CPC . H04R 3/00; H04R 3/02; H04R 25/00; H04R 25/45; H04R 25/453; H04R 29/00;
(Continued)

(56) References Cited

U.S. PATENT DOCUMENTS

2005/0101831 A1    5/2005  Miller, III et al.
2007/0167671 A1*   7/2007  Miller, III ............ H04R 25/606
                                                        600/25

(Continued)

OTHER PUBLICATIONS

International Search Report and the Written Opinion of the International Searching Authority, Application No. PCT/US2017/059444, dated Jan. 22, 2018, 12 pages.

(Continued)

*Primary Examiner* — Walter F Briney, III
(74) *Attorney, Agent, or Firm* — Sunstein LLP

(57) ABSTRACT

A noise cancelling system is described for a in a patient implantable hearing implant system. An implantable microphone senses a sound signal present at the microphone that includes a sound source component from a sound source external to the patient, and a noise component from internal bone conduction. At least one implantable noise sensing element is located near the microphone to sense the noise component. A filter is controlled by an adaptive algorithm responsive to transform the noise component and outputs a transducer control signal. A bone conduction transducer receives the transducer control signal and generates a corresponding mechanical vibration signal to the skull bone. The adaptive algorithm controls the filter so that the mechanical vibration signal of the bone conduction transducer offsets the noise component sensed by the at least one noise sensing element so as to minimize the noise component sensed by the implantable microphone.

16 Claims, 3 Drawing Sheets

(58) Field of Classification Search
CPC ............... H04R 29/001; H04R 29/004; H04R 2225/67; H04R 2410/00; H04R 2410/01; H04R 2410/05; H04R 2460/01; G10K 11/00; G10K 11/002; G10K 11/16; G10K 11/175; G10K 11/178; G10L 21/00; G10L 21/02; G10L 21/0202; G10L 21/0208
See application file for complete search history.

(56) References Cited

U.S. PATENT DOCUMENTS

| | | | |
|---|---|---|---|
| 2008/0192949 A1* | 8/2008 | Lin .................... | G10K 11/178 381/71.8 |
| 2009/0052698 A1 | 2/2009 | Rader et al. | |
| 2009/0112051 A1 | 4/2009 | Miller, III | |
| 2009/0187065 A1 | 7/2009 | Basinger | |
| 2010/0310084 A1 | 12/2010 | Hersbach | |
| 2011/0029041 A1 | 2/2011 | Wiskerke | |
| 2011/0319703 A1* | 12/2011 | Wiskerke ............... | H04R 25/30 600/25 |
| 2013/0096367 A1 | 4/2013 | Easter | |
| 2014/0003640 A1 | 1/2014 | Puria et al. | |
| 2016/0165362 A1 | 6/2016 | Hubert-Brierre et al. | |
| 2016/0217781 A1* | 7/2016 | Zhong .................... | H04R 17/00 |

OTHER PUBLICATIONS

Extended European Search Report, Application No. 17866724.2, dated Oct. 10, 2019, 7 pages.

* cited by examiner

ADAPTIVE NOISE CANCELLING OF BONE CONDUCTED NOISE IN THE MECHANICAL DOMAIN

This application claims priority from U.S. Provisional Patent Application 62/415,560, filed Nov. 1, 2016, which is incorporated herein by reference in its entirety.

FIELD OF THE INVENTION

The present invention relates to hearing implants, and more specifically to removing undesired noise from an implanted microphone signal in hearing implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes), which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea. In such cases a cochlear implant is an auditory prosthesis which uses an implanted stimulation electrode to bypass the acoustic transducing mechanism of the ear and instead stimulate auditory nerve tissue directly with small currents delivered by multiple electrode contacts distributed along the electrode.

FIG. 1 also shows some components of a typical cochlear implant system which includes an external microphone that provides an audio signal input to an external signal processing stage 111 where various signal processing schemes can be implemented. The processed signal is then converted into a digital data format, such as a sequence of data frames, for transmission into the implant stimulator 108. Besides extracting the audio information, the implant stimulator 108 also performs additional signal processing such as error correction, pulse formation, etc., and produces a stimulation pattern (based on the extracted audio information) that is sent through connected wires 109 to an implanted electrode carrier 110. Typically, this electrode carrier 110 includes multiple electrodes on its surface that provide selective stimulation of the cochlea 104.

In conventional hearing implant systems, an external microphone and signal processing are used as a much simpler option to implanting the microphone and/or signal processor under the skin with the other components of the system. Among the various challenges with using an implanted microphone is that in addition to the primary sound source signal that must be sensed through the skin, an implanted microphone also senses bone conducted noise that is present near the microphone. Such unwanted bone conducted noise is created by various bodily functions such as breathing, heartbeat, chewing, coughing and the like.

FIG. 2 depicts this situation where a subcutaneous microphone 201 senses the desired sound source signal s(n) received from a sound source external to the patient transcutaneous through the skin of the implanted patient, and also undesired bone conducted noise 202 n(n) due to for example chewing or speaking. Thus the microphone output signal represents a combination of these two signal sources, s(n)+n(n) which then must be further processed by an implanted signal processor.

One attempt to solve this problem tries to mechanically decouple the microphone from the skull bone by placing a sheet of soft material such as silicone between the bone and the microphone. But a subcutaneous microphone for a hearing implant system actually must be secured to the skull bone, so such decoupling cannot be perfect. This approach is described to some extent in U.S. Patent Publication 2005/0222487 by Miller, which is incorporated herein by reference.

Another approach as shown in FIG. 3 uses adaptive filtering where the output signal of the subcutaneous microphone 201 passes through a finite impulse response (FIR) filter 303 that is controlled by an adaptive algorithm 303 responsive to a signal from a second microphone or accelerometer 301 near the subcutaneous microphone 201 that senses the bone conducted noise 202 (but not the external sound source signal). This idea is described, for example, in U.S. Patent Publication 2010/0310084 by Hersbach, and U.S. Patent Publication 2008/0132750 by Miller, both of which are incorporated herein by reference.

Another approach to solve this problem in a hearing implant including a motion sensor and a bone-conduction transducer, such as a middle-ear hearing prosthesis is described in EP2624597 by Miller which is incorporated herein by reference. This approach has the disadvantage, that a transfer-function has to be determined by measurement and is due to the filter coefficient estimation prone to inaccuracies, back-coupling and less efficient body noise cancellation. Further, the transfer-function may be re-estimated and operation has to be suspended during re-estimation to attain noise-cancellation properties.

It is an object of the present invention to overcome the disadvantages from known systems and to provide a hearing implant part of a cochlear implant system comprising an microphone and an electromagnetic output transducer and a method for noise cancelling for a hearing implant. It is a further object of the invention to provide for a corresponding implantable microphone and a method for noise cancelling.

SUMMARY OF THE INVENTION

Embodiments of the present invention are directed to a noise cancelling system for in a patient implantable hearing implant system. An implantable microphone is configured to sense a sound signal present at the microphone and produce a corresponding microphone output signal for the hearing implant system. The sound signal includes a sound source component present at the microphone from a sound source external to the patient, and a noise component present at the microphone from internal bone conduction. There is at least one implantable noise sensing element that is located near the microphone and configured to sense the noise component. A filter is controlled by an adaptive algorithm responsive to transform the noise output signal provided from the at least one noise sensing element for output as transducer control signal. A bone conduction transducer is coupled to the filter output and to skull bone, and is configured to receive the transducer control signal and generate a corresponding mechanical vibration signal to the skull bone. The adaptive algorithm controls the filter so that the mechanical vibration signal of the bone conduction transducer offsets the noise component sensed by the at least one noise sensing element so as to minimize the noise component sensed by the implantable microphone.

In some specific embodiments there may be a transducer control amplifier between the filter and the bone conduction transducer that is configured to amplify the transducer control signal for input into the bone conduction transducer. The at least one implantable noise sensing element may include two separate noise sensing elements including a first noise sensing element configured to sense the noise component as an input for the adaptive algorithm, and a second noise sensing element configured to sense the noise component as an input for the filter. And the at least one implantable noise sensing element may specifically be a noise sensing accelerometer or a noise sensing microphone. The filter may be a digital IIR or FIR-filter.

Embodiments also include a complete hearing implant system having a microphone noise cancelling system according to any of the above; for example a cochlear implant system.

DETAILED DESCRIPTION OF SPECIFIC EMBODIMENTS

Various embodiments of the present invention are directed to arrangements for cancelling bone conducted noise sensed by an implanted microphone in the mechanical domain rather than in the electrical domain. A noise sensing element is placed close to or within the subcutaneous implanted microphone and the noise sensing element signal is used as an input to an adaptive algorithm that controls a filter where the filter input signal is coming from the first or a second noise sensing element that (also) senses the noise signal component. The filter output is used to drive a bone conduction transducer that generates a local vibrational "antinoise" that cancels the bone conducted noise and thus creates a spot of "vibrational silence" at the location of the microphone.

Figure 1:
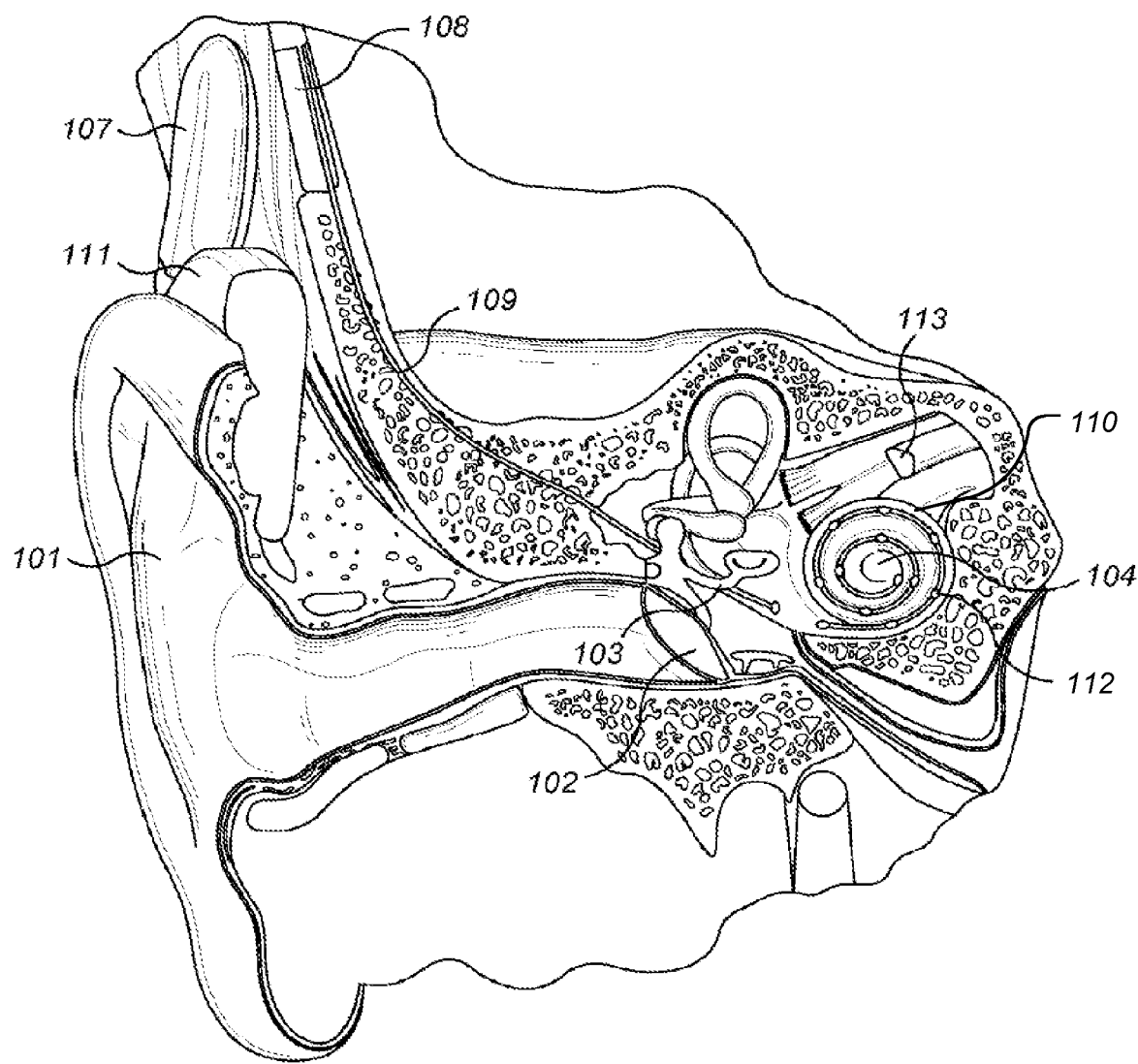
FIG. 1 shows elements of a human ear having a typical cochlear implant system.
Figure 2:
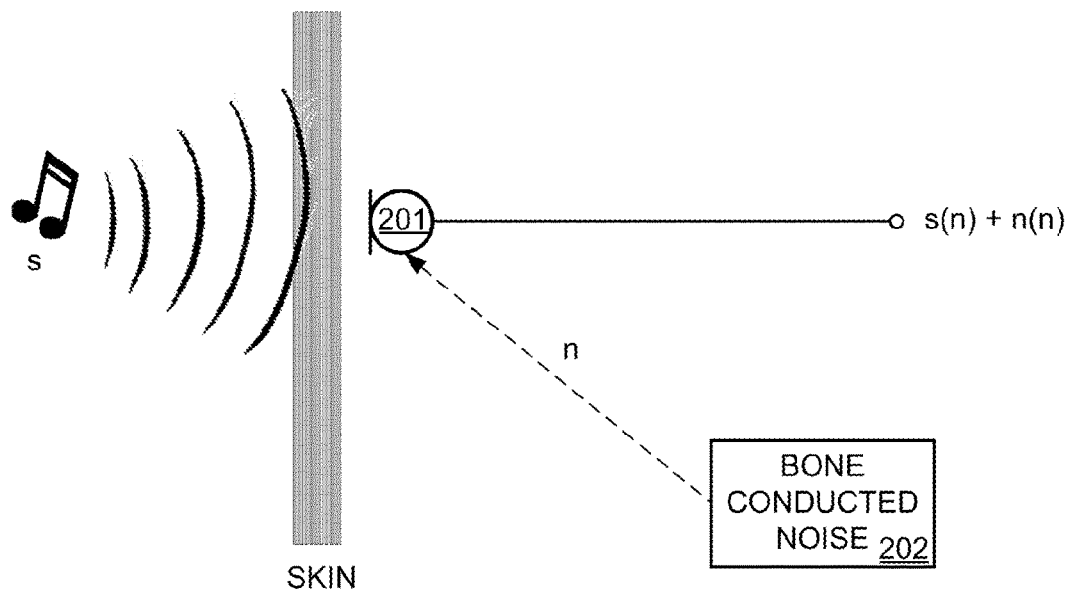
FIG. 2 shows how a subcutaneous microphone senses both an external primary sound source signal and internal bone conducted noise.
Figure 3:
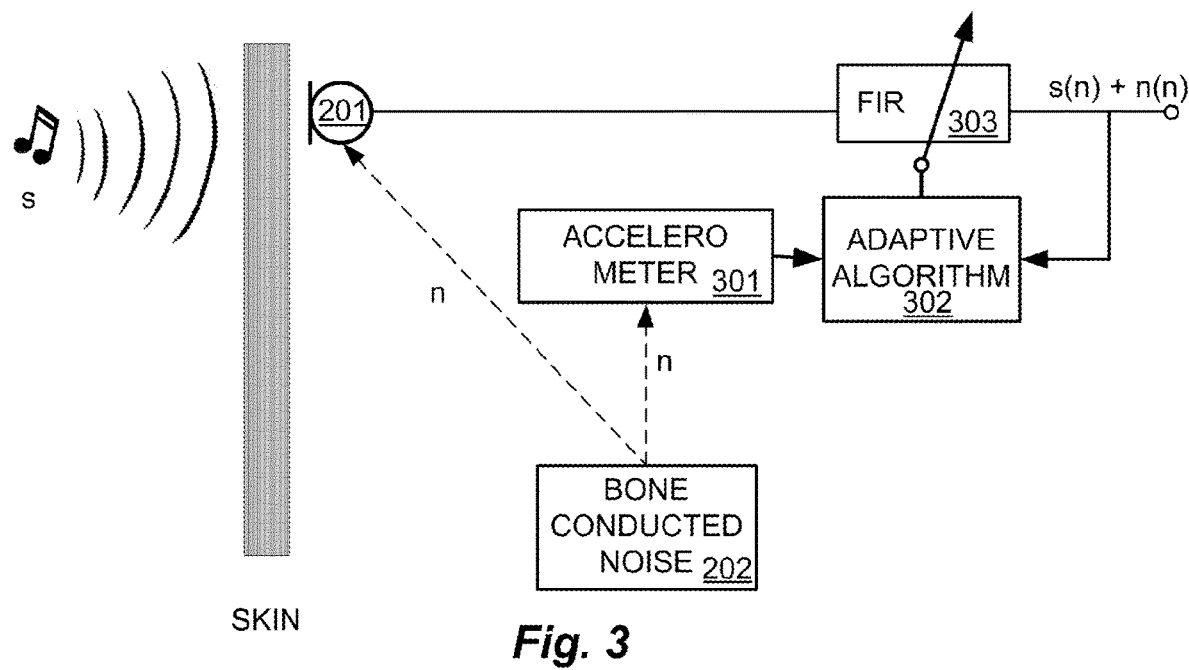
FIG. 3 shows use of an adaptive filter with a subcutaneous microphone to cancel bone conducted noise.
Figure 4:
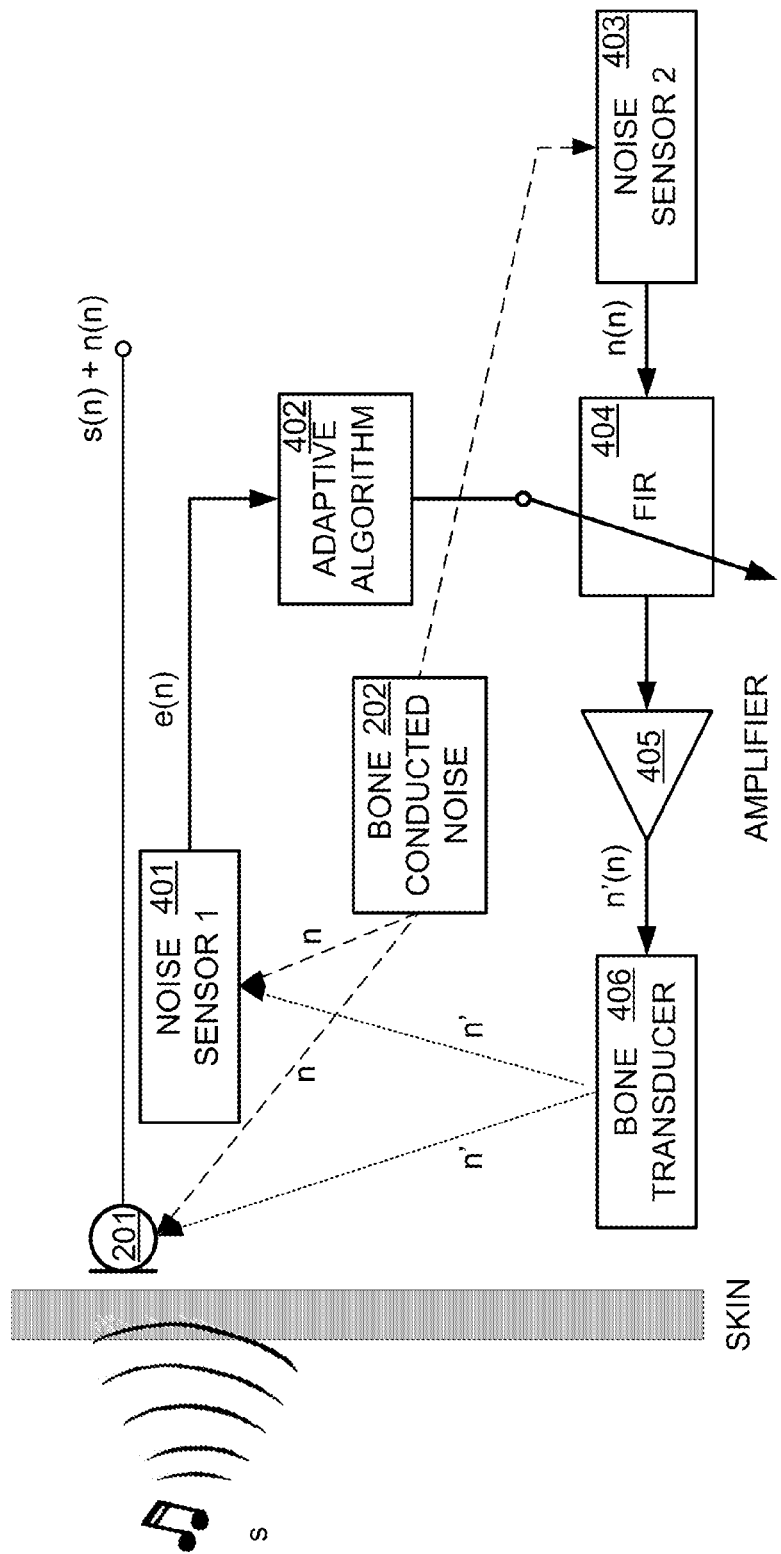
FIG. 4 shows use of a bone conduction transducer responsive to an adaptive algorithm to mechanically cancel the undesired bone conduction noise present at the implanted microphone according to an embodiment of the present invention.

FIG. 4 shows use of a bone conduction transducer responsive to an adaptive algorithm to mechanically cancel the undesired bone conduction noise present at an implanted microphone 201 that senses a sound signal present at the microphone and produce a corresponding microphone output signal for the hearing implant system according to an embodiment of the present invention. As discussed above, the sound signal sensed by the implanted microphone 201 includes a desired sound source component from a sound source external to the patient and a noise component from an undesired internal bone conduction noise 202. There also is one or more noise sensors located near the implanted microphone 201 arranged to sense the noise component (but not the sound source component). In the specific embodiment shown in FIG. 4, there are two such noise sensing elements 401 and 402. These may be separate devices, or two elements combined together in a single physical package, or a single sensor element may be used to produce the required noise sensing signals. The noise sensing element may specifically be a noise sensing accelerometer. Or a noise sensing microphone may be used with its sensing membrane arranged to face against the underlying skull bone rather than the overlying skin from which comes the sound source signal.

A filter 404 receives the noise component sensed by the first 401 or second noise sensing element 403 and is controlled by an adaptive algorithm 402 responsive to the noise component sensed by the first noise sensing element 401. Providing the noise component to filter 404 from the second noise sensing element 403 improves the stability by avoiding positive back-coupling and resonance effects. The output of the filter 404 is a transducer control signal that may be amplified by transducer control amplifier 405. The output of the transducer control amplifier 405 drives a bone conduction transducer 406 that is coupled to the skull bone and generates a corresponding mechanical vibration signal to the skull bone. The bone conduction transducer 406 may be located near the implanted microphone 201.

The adaptive algorithm 402 controls the filter 404 so that the mechanical vibration signal (n') of the bone conduction transducer 406 offsets the noise component (n) sensed by the first noise sensing element 401 so as to minimize the noise component sensed by the implantable microphone 201. This approach cancels the bone conduction noise in the mechanical domain before it is sensed by the implanted microphone 201 rather than later in the electrical domain of the microphone output when the noise component has already contaminated the primary sound source signal. The adaptive algorithm 402 may control the filter 404 by the filter coefficients. In the following a signal model with the noise component represented by E(n) in accordance to FIG. 4 as picked up by the microphone 201 and sound sensing element 401 is explained. The noise sensing element 401 may have a transfer function N(n), the bone conduction transducer 406 may have a transfer function B(n), the filter may have a transfer function F(n) and the head related transfer function from the location of the bone conduction transducer 406 to the location at the noise sensing element 401 may be H(n). The signal output Y(n) and given the input signal N(n) by the bone conduction transducer 406 can then be modeled by:

$$Y(n)=N(n)+H(n)B(n)FIR(n)E(n)N(n)$$

The filter transfer function F(n) has to be set in the way that the noise signal component N(n) is cancelled out, i.e. F(n)=1/H(n)B(n)E(n). None of the transfer functions are known and furthermore may change over time. With the arrangement and adaptive algorithm 402 according an embodiment of the invention, there is no need to estimate any of the transfer functions and further, there is no need to interrupt normal operation for generating reference signals to estimate transfer functions.

The adaptive algorithm 402 may for example operate according the homodyne detection principle. The signal e(n) is mixed with a reference signal of pre-defined frequency f, preferably a sine-wave signal. The mixed signal is low pass filtered or integrated over time, defining the homodyne output signal. The reference signal is phase shifted, until the homodyne output signal reaches the maximum. This may for example be achieved with a frequency modulated reference signal f±Δf and phase-adjustment based on the first order derivative of the homodyne output signal. The first order derivative is zero and therefore the phase adjustment vanishes at the maximum signal of the homodyne output signal. The thus measured maximum homodyne output signal and phase shift define the amplitude and phase shift respectively for the given frequency f. This measurement may be repeated for some or all the frequencies over the audible sound signal, for example and without limitation from 50 Hz to 20.000 Hz in steps of 50 Hz. The filter coefficients of the filter are then calculated based on the measured and negated amplitudes and the phase-shifts that reflect the desired filter transfer function according known techniques. Alternatively for the calculation of the filter coefficients instead of negated amplitudes, the phase-shift may be changed by 180°. The negated amplitude or phase shift is needed for obtaining a filter transfer function that offsets the noise component. The adaptive algorithm 402 is independent of any transfer function modeling wave-propagation and may be used during and without interrupting normal operation to dynamically adapt the filter coefficients and thereby control the filter. The filter may be a FIR or IIR filter or a combination of both. The adaptive algorithm 402 is very efficient in terms of computation complexity and energy consumption compared to for example fast-Fourier frequency analysis, that may be used instead of the before described homodyne principle.

Although various exemplary embodiments of the invention have been disclosed, those skilled in the art will appreciate that various changes and modifications can be made without departing from the true scope of the invention.

What is claimed is:

1. A noise cancelling arrangement in an implantable hearing implant system, the arrangement comprising:
   an implantable microphone configured to sense a sound signal present at the microphone and produce a corresponding microphone output signal for the hearing implant system, wherein the sound signal includes:
   i. a sound source component present at the microphone from a sound source external to the patient, and
   ii. a noise component present at the microphone from internal bone conduction;
   at least one implantable noise sensing element located at the microphone and configured to sense the noise component and produce a corresponding noise output signal;
   a filter controlled by an adaptive algorithm responsive to transform the noise output signal provided from the at least one noise sensing element for output as transducer control signal, wherein the transducer control signal is not based on, and is independent of, the microphone output signal;
   a bone conduction transducer coupled to the filter output and to skull bone, and configured to receive the transducer control signal and generate a corresponding mechanical vibration signal to the skull bone; and
   an implantable stimulator for providing a stimulation signal based on the microphone output signal,
   wherein the adaptive algorithm controls the filter so that the mechanical vibration signal of the bone conduction transducer offsets the noise component sensed by the at least one noise sensing element so as to minimize the noise component sensed by the implantable microphone.

2. The arrangement according to claim 1, further comprising:
   a transducer control amplifier between the filter and the bone conduction transducer configured to amplify the transducer control signal for input into the bone conduction transducer.

3. The arrangement according to claim 1, wherein the at least one implantable noise sensing element comprises two separate noise sensors including:
   a first noise sensor configured to sense the noise component as an input for the adaptive algorithm;
   a second noise sensor configured to sense the noise component as an input for the filter.

4. The arrangement according to claim 1, wherein the at least one implantable noise sensor is a noise sensing accelerometer.

5. The arrangement according to claim 1, wherein the at least one implantable noise sensor is a noise sensing microphone with the sound sensing membrane facing the skull bone.

6. The arrangement according to claim 1, wherein the hearing implant system is a cochlear implant system.

7. The arrangement according to claim 1, wherein the filter is a digital FIR-filter.

8. The arrangement according to claim 1, wherein the filter is a digital IIR-filter.

9. A method of noise cancelling for a hearing implant system implanted in a patient, the method comprising:
   sensing a sound signal present at an implantable microphone to produce a corresponding microphone output signal for the hearing implant system, wherein the sound signal includes:
   i. a sound source component present at the microphone from a sound source external to the patient, and
   ii. a noise component present at the microphone from internal bone conduction;
   sensing the noise component with at least one implantable noise sensor located at the microphone;
   controlling a filter with an adaptive algorithm responsive to transform the noise output signal provided from the at least one noise sensing element for output as transducer control signal, wherein the transducer control signal is not based on, and is independent of, the microphone output signal;
   receiving the transducer control signal at a bone conduction transducer coupled to skull bone and generating a corresponding mechanical vibration signal to the skull bone; and
   providing a stimulation signal based on the microphone output signal,
   wherein the adaptive algorithm controls the filter so that the mechanical vibration signal of the bone conduction transducer offsets the noise component sensed by the at least one noise sensing element so as to minimize the noise component sensed by the implantable microphone.

10. The method according to claim 9, further comprising:
    amplifying the transducer control signal for input into the bone conduction transducer.

11. The method according to claim 9, wherein the at least one implantable noise sensor comprises two separate noise sensing elements including:
    a first noise sensing element configured to sense the noise component as an input for the adaptive algorithm;
    a second noise sensing element configured to sense the noise component as an input for the filter.

12. The method according to claim 9, wherein the at least one implantable noise sensing element is a noise sensing accelerometer.

13. The method according to claim 9, wherein the at least one implantable noise sensing element is a noise sensing microphone.

14. The method according to claim 9, wherein the hearing implant system is a cochlear implant system.

15. The method according to claim 9, wherein the filter is a digital IIR or FIR-filter.

16. A hearing implant system using a noise cancelling method according to any of claims 9-15.

* * * * *